United States Patent [19]

Kurz

[11] 4,260,374
[45] Apr. 7, 1981

[54] ORTHODONTIC ELASTIC LIGATURE APPLICATOR FOR LINGUAL ORTHODONTIC APPLIANCES

[76] Inventor: Craven H. Kurz, No. 6 North Star, Apt. 106, Marina del Rey, Calif. 90291

[21] Appl. No.: 120,157

[22] Filed: Feb. 11, 1980

[51] Int. Cl.³ ............................ A61C 3/00; A61C 7/00
[52] U.S. Cl. .......................................... 433/3; 433/141
[58] Field of Search .................... 433/3, 15, 141, 164, 433/90; 221/290, 292, 293

[56] References Cited

U.S. PATENT DOCUMENTS

| 2,603,871 | 7/1952 | Call | 433/164 |
|---|---|---|---|
| 2,696,048 | 12/1954 | Lindgren | 433/164 |
| 3,475,818 | 11/1969 | Abrams | 433/3 |
| 3,861,045 | 1/1975 | Canter et al. | 433/3 |
| 4,001,940 | 1/1977 | Cusato | 433/3 |
| 4,040,187 | 8/1977 | Cardena | 433/3 |

Primary Examiner—Gene Mancene
Assistant Examiner—John J. Wilson
Attorney, Agent, or Firm—Keith D. Beecher

[57] ABSTRACT

An orthodontic hand tool is provided for inserting elastic ligatures into arch wire support brackets and tubes which are positioned on the lingual side of a patient's teeth. The hand tool includes a tubular housing which has a U-shape, so that when the housing is inserted into the mouth of the patient, the end of the housing may be placed against the lingual surface of a patient's tooth.

3 Claims, 4 Drawing Figures

ORTHODONTIC ELASTIC LIGATURE APPLICATOR FOR LINGUAL ORTHODONTIC APPLIANCES

BACKGROUND

My Copending Application Ser. No. 741,850 which was filed Nov. 15, 1976 for a Lingual Orthodontic Appliance discloses a lingual orthodontic arch wire appliance system which comprises a plurality of orthodontic brackets and tubes which are cemented directly to the lingual surfaces of the teeth of a patient, and an arch wire intercoupling the brackets and tubes extending around the lingual side of the teeth. The arch wire is supported on the bracket by means of individual annular elastic ligatures which are supported in grooves extending around the periphery of the respective brackets and tubes. The purpose of the present invention is to provide a hand tool which may be used conveniently to stretch and mount the annular elastic ligatures in the peripheral grooves of the various brackets and tubes so that they may support the arch wire.

The use of annular elastic ligatures in conjunction with orthodontic brackets and tubes is widespread and well established. However, the application of such ligatures to the brackets and tubes has represented a tedious and time consuming operation. Hand tools have been proposed in the past for applying elastic ligatures to the brackets and tubes, but such prior art hand tools have met with only limited acceptance, and none is appropriate for inserting the ligatures on orthodontic brackets and tubes which have been affixed to the lingual side of the teeth, as is the case with the appliance of the copending application.

In the case of the lingual brackets and tubes of the copending application, the operation of inserting the annular elastic ligatures is more complicated because of the inaccessible position of the brackets, and the objective of the present invention is to provide a hand tool which is particularly adapted to apply the annular elastic ligatures to the lingual brackets.

As mentioned above, the hand tool of the present invention is constructed of a particular shape to allow for easy placing of the ligatures on the brackets and tubes attached to the lingual surfaces of the patient's teeth. The appliance is constructed to be hand manipulated by the orthodontist so as to carry the ligature to the lingual surface of the tooth in position to be stretched around and into the peripheral channel in the lingual bracket in order to hold the arch wire in place.

DETAILED DESCRIPTION OF THE ILLUSTRATED EMBODIMENT

Figure 1:
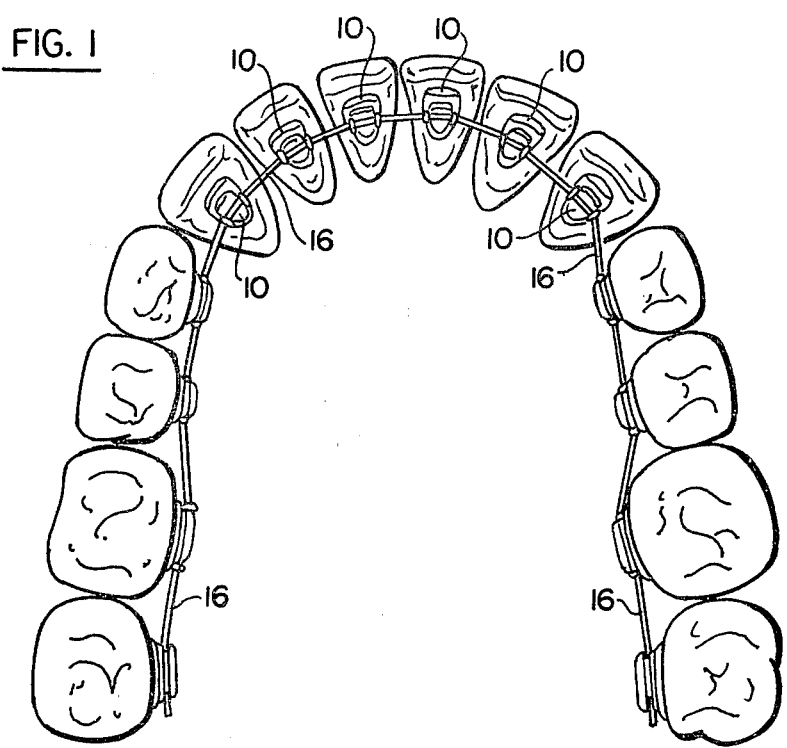
FIG. 1 is a plan view of the mandibular arch of a patient, and showing a direct bonded fixed lingual orthodontic arch wire appliance system, such as described in the copending application, in place on the lingual surfaces of the teeth forming the arch.

In the representation of FIG. 1, a direct bonded fixed lingual orthodontic arch wire appliance system, constructed in accordance with the invention described in the copending application, is shown with its orthodontic brackets and tubes adhesively attached to the lingual surfaces of the teeth forming the illustrated mandibular arch. The orthodontic appliance system of FIG. 1 includes a plurality of brackets 10 of the type shown in FIG. 2, and other brackets attached to other teeth of the arch. The brackets are adhesively attached to the lingual surfaces of the various teeth which make up the mandibular arch of FIG. 1.

Figure 2:
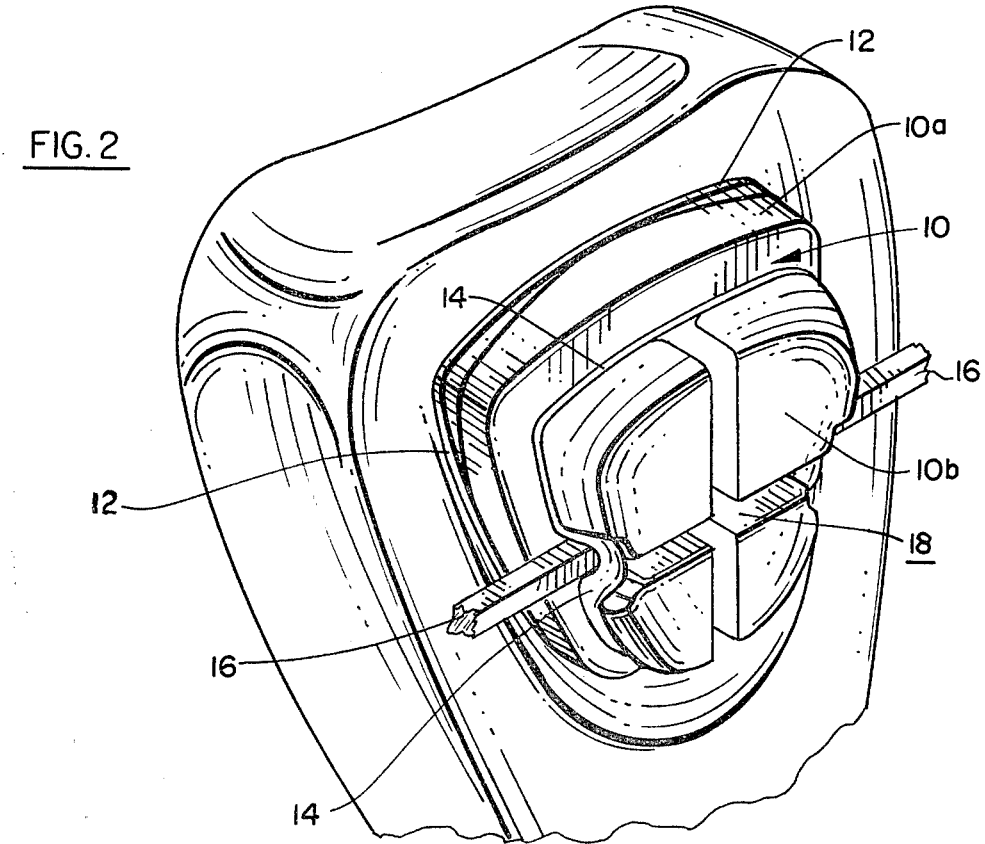
FIG. 2 is a perspective view of a lingual bracket suitable for use in conjunction with certain ones of the teeth forming the arch of FIG. 1.

As shown in FIG. 2, the bracket 10 is designed to fit between the lingual ridges of the corresponding tooth in intimate contact with the lingual tooth surface. The bracket includes a base portion 10a which is adhesively attached to the lingual surface of the tooth by an adhesive layer 12. The bracket also includes a portion 10b integral with the base 10a but of smaller dimensions than the base. A peripheral groove extends between the portion 10b and base 10a for receiving an annular elastic ligature 14 which serves to retain the arch wire 16 within a transverse slot 18 which extends across the portion 10b of the bracket.

Figure 3:
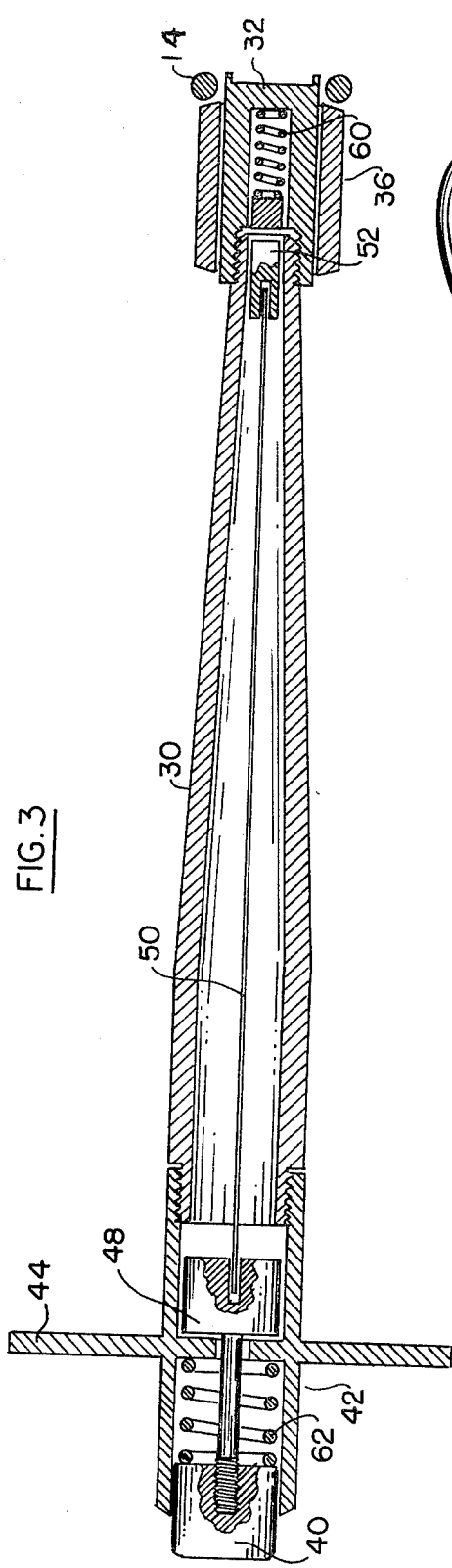
FIG. 3 is a side sectional view of a hand tool representing one embodiment of the invention.

As mentioned above, the present invention provides a hand tool for applying the ligatures 14 to brackets such as the bracket 10. One embodiment of the invention is shown in FIG. 3, and, as illustrated, the hand tool of FIG. 3 includes an elongated tubular housing 30 which has a support member 32 attached to one end, for example, by appropriate threads. One of the elastic ligatures 14 is supported in a stretched condition about the periphery of the support member 32 adjacent to its forward edge. The ligature 14 may be applied to the forward edge of the support member 32 either by hand, or by means of a mandibular type of hand tool, such as the hand tool described in my Copending Application Ser. No. 135,976 filed on Mar. 31, 1980.

An ejector 36 is slidably mounted on the support member 32 in coaxial relationship with the support member, and the ejector is adapted to be moved forward with respect to the support member to eject the ligature 14, and then to be moved back from the forward edge of the support member 32 to receive a new ligature.

The shape of the forward end of the support member 32 may be made to conform with the shape of the bracket or tube to which the ligature is to be applied, so that when the hand tool is inserted into the mouth of the patient with the forward end of the support member 32 adjacent to the surface of the corresponding bracket, the ligature 14 may be ejected into the peripheral channel to support the arch wire 16 as shown in FIG. 2.

A pushbutton 40 is mounted in a further housing 42 which, in turn, is mounted on the rear end of housing 30, for example, by a threaded connection, as shown. An appropriate annular finger stop 44 may be formed on the housing 42, so that the pushbutton 40 may be operated by supporting the fingers around stop 44 and pressing the button 40 by the operator's thumb. The pushbutton 40 is connected to a further member 48 which is slidable in the housing 42, and a push rod 50 couples the member 48 to a further member 52 at the other end of the tubular housing 30, the latter member serving as a push means for the ejector 36. The ejector 36 is spring biased against the forward end of member 52 by means of a spring 60, and the pushbutton 40 is spring biased to the rear of the housing 42 by a spring 62.

It is evident that when the push member 40 is depressed into the housing 42, the pusher 52 causes the ejector 36 to move forward on the support 60 to eject the ligature 14. Then, when the pushbutton is released, the springs 60 and 62 return the assembly to the position shown in FIG. 3.

Figure 4:
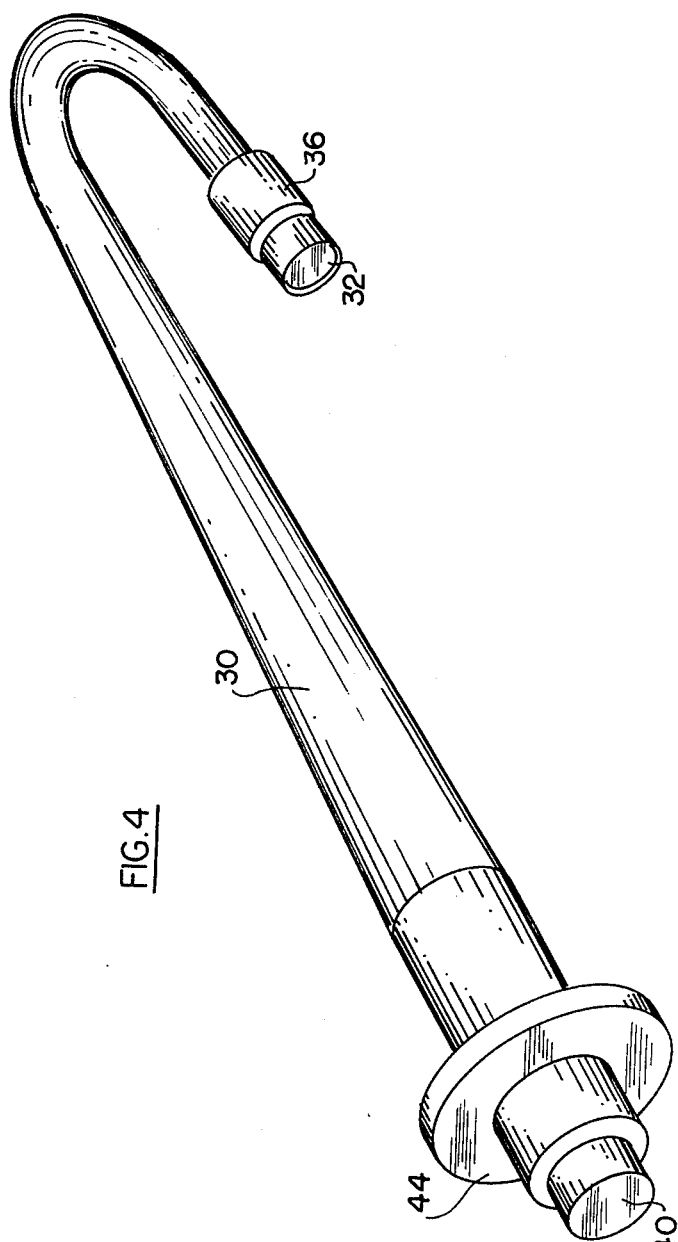
FIG. 4 is a perspective representation of the hand tool of FIG. 3 bent into a U-shape so as to perform its intended function.

The tubular member 30 is formed of an appropriate flexible plastic, or other appropriate flexible material, so that it can be bent into the configuration shown in FIG. 4, so that the forward end of the support member 32 may be placed against any selected one of the lingual brackets or tubes in FIG. 1. Then, when the pushbutton 40 is depressed, the ligature is ejected onto the bracket or tube and into the peripheral channel to support the arch wire 36. The push rod 50 may be, for example, formed of spring steel so as to be resilient, and to be able to perform its function when the tubular member 30 is bent to the configuration of FIG. 4.

The invention provides, therefore, an improved hand tool which permits the orthodontist conveniently to insert annular elastic ligatures onto lingual orthodontic brackets and tubes. It will be appreciated that while a particular embodiment of the invention has been shown and described, modifications may be made. It is intended to cover such modifications in the following claims.

What is claimed is:

1. A hand tool for an orthodontist to permit the orthodontist to mount stretched annular elastic ligatures onto orthodontic arch wire support brackets affixed to the lingual side of the teeth of a patient, said hand tool comprising: an elongated tubular housing having a U-shape so that the forward end of the housing may be placed against the lingual surface of a tooth when the housing is inserted into the mouth of a patient; a support member positioned on the forward end of the housing for supporting an annular elastic ligature in a stretched condition about its periphery; an ejector member mounted on said support member in coaxial relationship therewith and reciprocally slidable on said support member; a pushbutton mounted on the rear end of said housing; a push rod coupling the pushbutton to the ejector member so that when the pushbutton is depressed, the ejector member moves forward on said support member to eject the annular elastic ligature; and spring means biasing said ejector member and said pushbutton towards the rear of said housing.

2. The hand tool defined in claim 1, in which said housing is formed of a flexible material to permit the housing to be bent into the U shape.

3. The hand tool defined in claim 2, in which said push rod is formed of a selected material to enable the push rod to exhibit resilient characteristics.

* * * * *